US 009859029B2

(12) United States Patent
Jia et al.

(10) Patent No.: US 9,859,029 B2
(45) Date of Patent: *Jan. 2, 2018

(54) X-RAY LASER MICROSCOPY SAMPLE ANALYSIS SYSTEM AND METHOD

(71) Applicant: Rising Star Pathway, a California Corporation, Cupertino, CA (US)

(72) Inventors: Allison Sihan Jia, Cupertino, CA (US); Muzhi Liu, Shen Zhen (CN); Yuhao Wang, Tang Shan (CN); Kevin Shaokang You, Palo Alto, CA (US); Jingyi Zhang, Beijing (CN); Zhuotong Xian, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/442,670

(22) Filed: Feb. 26, 2017

(65) Prior Publication Data

US 2017/0169910 A1 Jun. 15, 2017

Related U.S. Application Data

(63) Continuation-in-part of application No. 15/218,017, filed on Jul. 23, 2016, now Pat. No. 9,583,229.

(51) Int. Cl.
*G01N 23/00* (2006.01)
*G21K 7/00* (2006.01)

(52) U.S. Cl.
CPC ............... *G21K 7/00* (2013.01); *G01N 23/00* (2013.01); *G01N 2223/304* (2013.01); *G01N 2223/3103* (2013.01); *G01N 2223/316* (2013.01)

(58) Field of Classification Search
CPC ..... G01N 2223/3103; G01N 2223/304; G01N 2223/316; G01N 23/00; G01N 23/20083; G21K 7/00
See application file for complete search history.

(56) References Cited

U.S. PATENT DOCUMENTS 5,177,774 A * 1/1993 Suckewer ............... G21K 7/00
378/43
5,450,463 A * 9/1995 Iketaki ..................... G21K 7/00
378/43

(Continued)

OTHER PUBLICATIONS

Dennison et al. (1992) Ultrahigh vacuum chamber for synchrotron x-ray diffraction from films absorbed on single crystal surfaces; Rev. Sci. Instrum. 63(8). pp. 3835-3841.*

(Continued)

*Primary Examiner* — David J Makiya
*Assistant Examiner* — Soorena Kefayati
(74) *Attorney, Agent, or Firm* — Stephen E. Zweig

(57) ABSTRACT

Improved system and method of X-ray laser microscopy that combines information obtained from both X-ray diffraction and X-ray imaging methods. At least one sample is placed in an ultra-cold, ultra-low pressure vacuum chamber, often using a sample administration device configured to present a plurality of samples. The sample is exposed to brief bursts of coherent X-ray illumination, often further concentrated using X-ray mirrors and pinhole collimation methods. Higher resolution data from the samples is obtained using hard X-ray lasers, such as free electron X-ray lasers, and X-ray diffraction methods. Lower resolution data from the same samples can be obtained using any of hard or soft X-ray laser sources, and X-ray imaging methods employing nanoscale etched zone plate technology. In some embodiments both diffraction and imaging data can be obtained simultaneously. Data from both sources are combined to create a more complete representation of the samples.

20 Claims, 10 Drawing Sheets

(56) References Cited

U.S. PATENT DOCUMENTS

| | | | | |
|---|---|---|---|---|
| 6,333,967 | B1* | 12/2001 | Osaka | H01J 35/02 378/121 |
| 6,438,200 | B1* | 8/2002 | Kita | G01N 23/223 378/44 |
| 7,105,813 | B2* | 9/2006 | Lee | G01N 23/2258 250/281 |
| 7,620,148 | B2* | 11/2009 | Harel | G01N 23/207 378/70 |
| 7,835,499 | B2* | 11/2010 | Yu | H01J 25/02 378/119 |
| 8,001,853 | B2* | 8/2011 | Pratt | G01N 1/286 73/863 |
| 8,013,300 | B2* | 9/2011 | Stern | G01N 1/34 250/307 |
| 8,334,510 | B2* | 12/2012 | Shachal | G01N 23/22 250/306 |
| 8,382,301 | B2* | 2/2013 | Ehm | B82Y 10/00 359/850 |
| 8,450,683 | B2* | 5/2013 | Yamazaki | H01J 37/28 250/306 |
| 8,462,824 | B2* | 6/2013 | Popmintchev | G02F 1/353 372/21 |
| 8,513,603 | B1* | 8/2013 | Lederman | G01N 23/223 250/305 |
| 8,582,610 | B2* | 11/2013 | Krausz | G02F 1/3501 372/21 |
| 9,025,724 | B2* | 5/2015 | Lee | G01N 9/24 378/10 |
| 9,129,715 | B2* | 9/2015 | Adler | G01N 23/04 |
| 9,275,844 | B2* | 3/2016 | Bogan | H01J 49/0431 |
| 9,335,282 | B2* | 5/2016 | Omote | G01N 23/207 |
| 9,377,419 | B2* | 6/2016 | Las Navas Garcia | G01N 5/045 |
| 2011/0158379 | A1* | 6/2011 | Cheon | G21K 1/06 378/4 |
| 2014/0087321 | A1* | 3/2014 | Waniuk | F27B 14/061 432/13 |
| 2015/0110249 | A1* | 4/2015 | Bakeman | G01N 23/201 378/87 |
| 2015/0158125 | A1* | 6/2015 | Borgmann | B23K 31/02 228/104 |
| 2015/0168318 | A1* | 6/2015 | Beckman | H01J 49/0431 250/307 |
| 2015/0373821 | A1* | 12/2015 | Suzuki | H05G 1/025 378/62 |
| 2016/0320320 | A1* | 11/2016 | Yun | G01N 23/20075 |
| 2017/0146468 | A1* | 5/2017 | Mukaide | G01N 23/083 |

OTHER PUBLICATIONS

K.J. Gaffney, et. al., "Imaging Atomic Structure and Dynamics with Ultrafast X-ray Scattering", Science 316, 1444 (2007). Entire document.

Chang and Sadkinawat, "Ultra-high aspect ratio high-resolution nanofabrication for hard X-ray diffractive optics", Nature Communications 5:4243 (2014). Entire document.

Chao et. al., "Soft X-ray microscopy at a spatial resolution better than 15nm", Nature 435, Jun. 30, 2005, pp. 1210-1213. Entire document.

Kang, et. al., "Nanometer Linear Focusing of Hard X Rays by a Multilayer Laue Lens", Physical Review Letters 96, Mar. 31, 2006, pp. 127401-1-127401-4. Entire document.

\* cited by examiner

X-RAY LASER MICROSCOPY SAMPLE ANALYSIS SYSTEM AND METHOD

CROSS REFERENCE TO RELATED APPLICATIONS

This invention is a continuation in part of U.S. patent application Ser. No. 15/218,017 "IMPROVED X-RAY LASER MICROSCOPY SYSTEM AND METHOD", filed Jul. 23, 2016, now U.S. Pat. No. 9,583,229, issued Feb. 28, 2017; the entire contents of this application are incorporated herein by reference.

BACKGROUND OF THE INVENTION

Field of the Invention

This invention is in the field of X-ray laser microscopy.

Description of the Related Art

The resolving power of conventional optical microscopes is limited by the wavelength of light. Thus over the years, various methods employing shorter wavelength particles, such as electrons, and shorter wavelength photons, such as X-rays, have been employed to achieve still higher levels of resolution.

X-ray radiation spans a range of wavelengths in the nanometer region, generally ranging from about 10 nanometers (soft X-rays) with energies of around 100 electron volts, to about 0.01 nanometers (hard X-rays) with energies up to about 10,000 electron volts. Photons with energies above this are typically referred to as gamma rays. Since many molecular biological structures of interest have structural details in roughly the 10 to 0.1 nanometer range, scientists have turned to X-rays to help elucidate the structure of proteins, DNA, membranes, viruses, cells, and other biological structures of interest.

Due to the desirable aspects of coherent light sources, X-ray lasers are particularly useful for X-ray microscopy. Here various methods have been employed, including X-ray diffraction methods, X-ray holographic methods, and various types of X-ray imaging methods. Although X-ray mirrors and lenses are much more difficult to fabricate than their optical counterparts, various methods of focusing X-rays, including Wolter, Kirkpatrick-Baez, and Schwarzschild x-ray mirror designs, as well as various types of zone plate methods (which operate according to diffraction methods) have been devised.

Some recent improvements in zone plate technology include the work of Chang and Sakdinawat, "Ultra-high aspect ratio high-resolution nanofabrication for hard X-ray diffractive optics" NATURE COMMUNICATIONS, 5:4243, Jun. 27, 2014, pages 1-7 (DOI: 10.1038/ncomms5243). They taught that improved zone plates can be produced using some of the same photolithographic methods used to produce modern integrated circuits and other nanostructures. These methods are also described by their US patent application 2015/037679.

Previous work in the X-ray microscopy field includes the soft X-ray imaging methods of Suckwer et. al., U.S. Pat. No. 5,177,774; Chao et. al, "Soft X-ray microscopy at a spatial resolution better than 15 nm", NATURE, Vol 435, Jun. 30, 2005, pages 1210 to 1213; and Kirtz et. al., "Soft X-ray microscopes and their biological applications", Q. Rev. Biophys. 28, 33-130 (1995).

Other workers have used ultra-short bursts of hard X-rays, often produced by free electron lasers, and X-ray diffraction methods, to elucidate structures at still higher resolution. This work includes Gaffney et. al., "Imaging Atomic Structure and Dynamics with Ultrafast X-ray Scattering", Science 316, Jun. 8, 2007, pages 1444-1448.

Despite these advances, the field remains challenging. The highest resolution laser microscopy sample details can generally only be obtained by using ultra-short hard X-rays, which are difficult to focus, and which tend to rapidly destroy the sample. Here, use of X-rays produced by free electron lasers, ultra-short bursts of energy, and X-ray diffraction methods (which do not require the sample scattered X-rays to be imaged) are favored.

By contrast, lower resolution laser microscopy, using soft X-rays, is a bit closer to conventional microscopy. Coherent soft X-ray light can be produced by a variety of different methods, and the lower energies tend to be less destructive of the sample. The soft X-rays, after being scattered by the sample, can be focused by various methods, such as various phase zone plate methods, resulting in a more conventional type magnified image of the sample.

Another problem is that the performance of existing X-ray laser microscopes can be limited by other effects, such as X-ray scattering or attenuation off of residual air molecules in the vacuum chamber, and by thermal effects (e.g. heating of the sample and X-ray lenses).

Another problem is sample administration. Although some prior art methods, such as the methods of Gaffney, are configured to analyze more than one sample by sending particle stream composed of a plurality of single particles through the X-ray beam, such methods can have drawbacks.

BRIEF SUMMARY OF THE INVENTION

The invention is based, in part, on the insight that the lower resolution sample structural information produced by prior art hard X-ray laser systems, which rely on X-ray laser diffraction methods, is frequently lost. This is because larger (e.g. lower resolution) sample structural details do not end up substantially diffracting the angle of the X-ray laser beam. Instead, larger sized structural details only cause the X-rays to be diffracted at low angles from the main X-ray beam. Thus these larger sample structural details are not well separated from X-rays that pass completely through the sample (116) to any significant extent. This often shows up as the central "sun" in a "sunburst" type X-ray diffraction pattern. As an example, see Gaffney and Chapman, Science 316, 1444 (2007), FIG. 3A and 3B, which illustrate how the center region of an X-ray diffraction pattern is essentially unreadable.

This invention is also based, in part, on the insight that this missing low resolution structural information could be provided by use of alternative X-ray imaging methods, such as phase zone plate methods, and that if the phase zone plate was positioned in an X-ray diffraction apparatus so that the phase zone plate only obscured a small portion of the center of the X-ray diffraction detector, little X-ray diffraction information would be lost because, as discussed above, the central portion of an X-ray diffraction detector has little value due to interference from the main X-ray beam that has passed completely through the sample.

The invention is also based, in part, on the insight that in this regard, advances in high-resolution nanofabrication methods have allowed for the fabrication of ultra-small zone plates capable of focusing even hard X-rays, as well as soft X-rays. Collimator devices with ultra-small (nanometer scale) collimator openings may also be produced using these methods.

The invention is also based, in part, on the insight that for higher performance, every effort must be made to reduce the damaging effects of X-ray beams on both the sample and on the various X-ray microscope components. In this regards, greater efforts to chill the devices to ultra-cold temperatures, by use of cryogenic fluids, possibly including even liquid helium, would be desirable. Further, to improve contrast, every effort must also be made to reduce the vacuum of the microscopy chamber to unusually low pressure levels.

The invention is also based, in part, on the insight that improved methods of sample handing and administration would also be useful. Ideally the system should be able to handle multiple types of samples in a single run. Thus, as will be discussed, in some embodiments, the method may also use a sample dispensing device, such as an automated dispensing device, configured to present a plurality of samples, which may be different types of samples, and analyze this plurality of different samples during a single observing session. Such X-ray microscopy facilities are typically quite expensive, and use of improved dispensing devices and methods, configured for more optimal methods of sample delivery, can allow for more rapid data collection during a given microscopy session. This in turn makes such X-ray microscopy facilities more feasible for high volume use, and can open up the use of facilities to handle a greater variety of research problems in a more cost effective manner.

Thus in some embodiments, the invention may be an improved X-ray laser microscopy method, equipped to analyze a given sample (and often a plurality of given samples) using (sometimes simultaneously) both X-ray diffraction and X-ray imaging methods onto different X-ray detector regions. Typically the higher resolution sample data will be obtained from the X-ray diffraction portion of the device, while the lower resolution sample data will be obtained from the X-ray imaging portion of the device. Both the X-ray diffraction data and the X-ray imaging data can be fed to a computer, which can be configured to use both sets of information to produce a combined view of the sample that provides more structural information than either one method could produce by itself.

To obtain X-ray imaging data with minimum loss of X-ray diffraction data, and with as short a wavelength of X-ray radiation as possible, the system may often make use of nanoscale etched zone plate technology.

The efficiency of the improved X-ray microscope can further be enhanced by chilling various portions of the device to ultra-low temperatures, and maintaining ultra-low vacuum during operation.

This method will typically use at least one X-ray laser providing coherent X-rays through an X-ray port (or other opening) into a vacuum chamber. Inside the vacuum chamber, a first X-ray optical device, such as an X-ray mirror device, will focus or collimate the coherent X-rays onto the sample.

Improved sample handling techniques, to enable higher sample throughput, will also be taught.

DETAILED DESCRIPTION OF THE INVENTION

Figure 1:
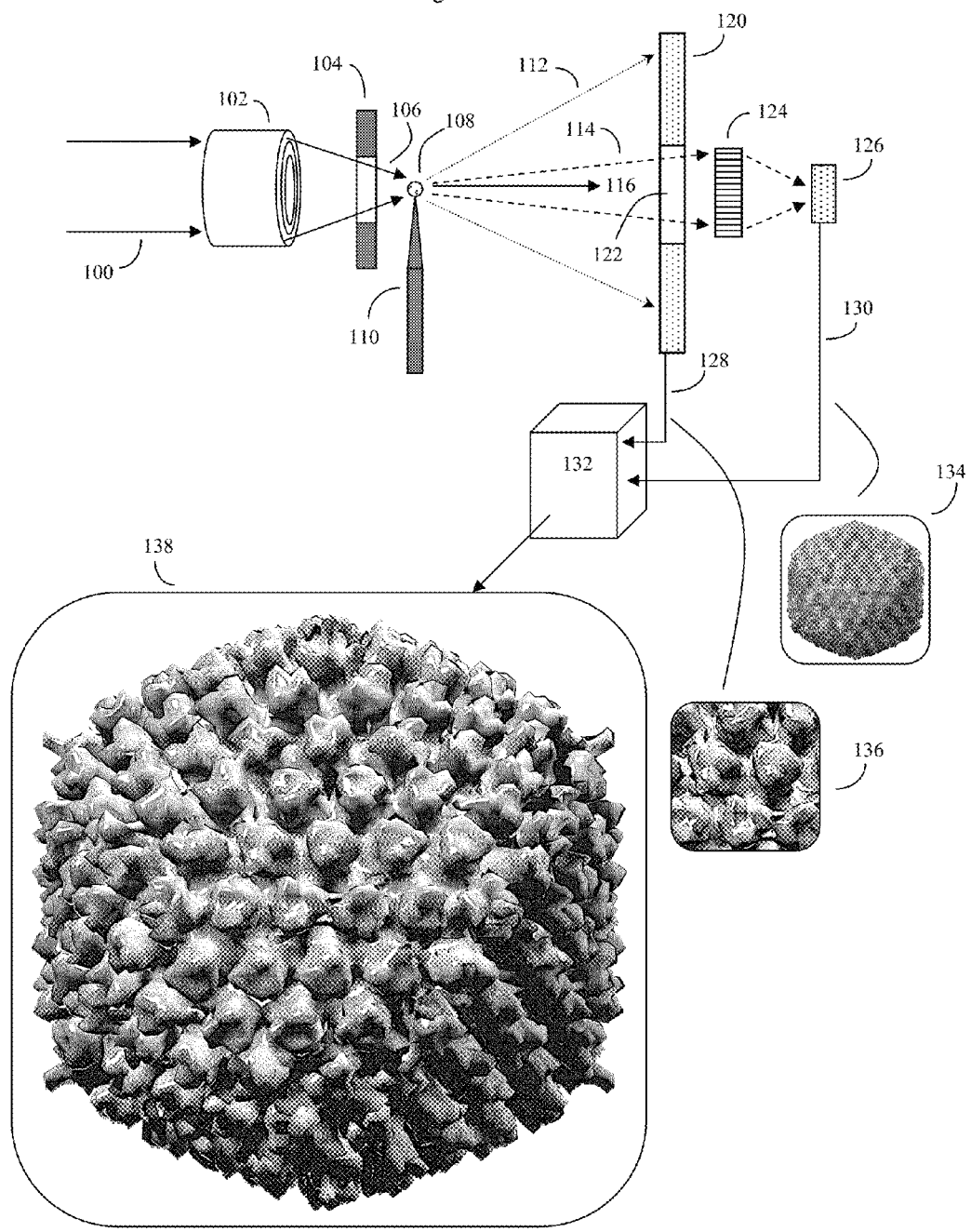
FIG. 1 shows an overview of the improved X-ray laser microscopy method.
Figure 4:
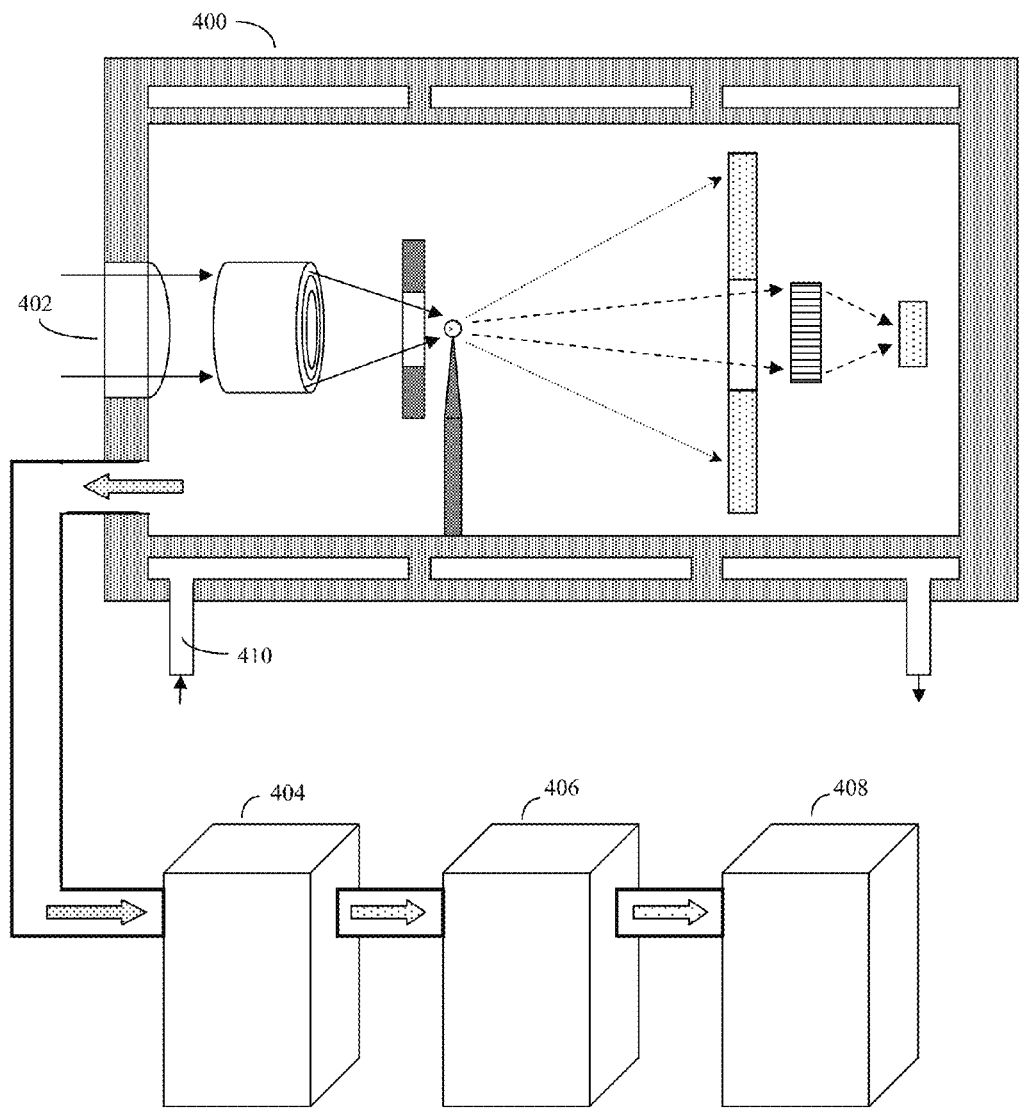
FIG. 4 shows some additional components, such as a vacuum chamber, that are also used in the improved X-ray laser microscopy method.

Here it will be useful to refer to both FIG. 1 and FIG. 4.

FIG. 1 shows an overview of the improved X-ray laser microscopy method, while FIG. 4 gives more details about the microscope's vacuum chamber, vacuum pump system, and X-ray port arrangement.

In some embodiments, the invention may be a system, device or method of X-ray laser microscopy, typically using at least one X-ray laser (not shown), which will supply a coherent source of X-ray illumination (100), typically through an X-ray port (402) into a vacuum chamber (400) configured to hold many of the other X-ray microscope components. In the following description, unless otherwise specified or drawn, assume that the various methods and components that are described are inside of a vacuum chamber (400).

Note that typically the X-ray port will be composed of a substantially vacuum tight but X-ray resistant material. However in the case where the X-ray laser itself is under the same vacuum conditions as the vacuum chamber, then the X-ray port may be a simple opening in the side of the vacuum chamber.

This coherent source of X-ray illumination can be provided by various types of X-ray lasers, and indeed in some embodiments, it may be useful to use more than one type of X-ray laser (e.g. a hard X-ray laser and a soft X-ray laser).

These X-ray lasers can be any of a free-electron laser, capillary plasma-discharge laser, solid-slab target laser, optical field excited plasma laser, high-harmonic generation laser, and the like.

Since the beam size of coherent X-ray light sources (100) is usually significantly larger than the size of the microscopy sample (108), it will typically be useful to use a first X-ray optical device (102) configured to focus and/or collimate the X-rays onto the microscopy sample (sample) (108). A sample administrator (110) will control the position of the sample.

X-rays (106) focused by the first X-ray optical device (102) typically impinge on the sample (108), where some X-rays (112, 114) are scattered or diffracted at various angles by the sample, while other X-rays pass (116) completely through the sample on their original paths without any significant deflection. At least some of these X-rays (e.g. at least 112) are in turn detected by a detection apparatus (120). Typically, the configuration of the X-ray microscope inside the vacuum chamber is such that the first X-ray optical device (102) is disposed in between the X-ray port (402) and the sample (108) (e.g. sample position controlled by the sample administrator 110), and the sample (again as controlled by the sample administrator 110) is substantially in between the first X-ray optical device (102) and the detection apparatus (112).

This first X-ray optical device (102), as well as optionally the second X-ray optical device (124) will typically comprise at least one X-ray mirror formed from a plurality of curved X-ray reflecting surfaces. Here, X-ray mirror designs such as various Wolter, Kirkpatrick-Baez, or Schwarzschild x-ray mirror designs may be used.

In some embodiments, at least the exposed mirror surfaces of these X-ray mirror designs may comprise X-ray resistant, X-ray reflecting materials, such as silicon, boron, silicon triboride, and the like.

As will be discussed shortly, the detection apparatus may contain more than one portion (e.g. detection region). Usually the detection region will comprise at least a first outer region (120) configured to detect both the location and intensity of various X-rays (112) that have been diffracted away from the main X-ray beam (116).

Use of three stage vacuum pumps: In operation, to reduce interference from air molecules, which can both absorb and scatter the coherent X-rays, thus reducing microscopy performance, the pressure inside the vacuum chamber (400) will typically be reduced to very low pressures, often on the order of $10^{-9}$ Torr or less, usually by using at least one exterior vacuum pump system (e.g. 404, 406, 408). This system may be a multiple stage vacuum pump. For example, a three stage vacuum pump system, where the first stage may be a positive displacement pump, the second stage may be a sorption pump, and the third stage may be any of a cryopump, turbo molecular pump, and/or an ion pump may be used.

The sample administrator (110) will be used to control the position of the microscopy sample(s) (108). In some embodiments, such as when the sample administrator (110) holds the sample (108) on the end of a pin like structure, the sample may be introduced to the vacuum chamber (400) before the pressure is reduced. In other configurations, such as when the sample administrator is used to inject or place the sample into the vacuum chamber at a defined location, the sample may be introduced into the vacuum chamber after the vacuum has been reduced.

Various methods may be used to inject or place the sample. The sample may be placed into position at the end of a simple pin-like holder, or more complex robotic sample handing device. Alternatively the sample may be injected as a stream of small moving particles, as per the methods of Gaffney, Science 316, 1444 (2007).

The X-rays used in this microscopy method are very energetic, and can heat X-ray optical elements (e.g. mirror systems 102, zone plates 124, etc.) to high temperatures. This heating is undesirable, both from the standpoint of preserving the structure of the X-ray optical elements (102, 124), as well as in causing undesired frequency wavelength shifts in the X-rays interacting with the X-ray optical elements, thus reducing the resolution of the microscope. To reduce these effects, thus increasing both the lifetime and the performance of the various X-ray optical elements, it will often be useful to chill at least some of the various X-ray optical elements (102, 124) to low temperatures, preferably extremely low temperatures such as 20 degrees Kelvin or less.

In at least one mode of operation of the X-ray microscope, the system will use the X-ray port (402) to provide a very short burst of coherent X-rays (100), as well as use the first X-ray optical device (102) to focus and/or collimate this burst of coherent X-rays onto the microscopy sample (108) (position determined by the sample administrator 110). The system will then use at least the first portion of the detection apparatus (120, 120a) to detect a first signal from the sample. This first signal will be at least some of the spatially separated X-rays (112, 112a, 112b) that have been diffracted at various angles by the microscopy sample (108).

For at least hard X-ray lasers, very short bursts of illumination are preferable. This is because the X-ray burst will usually completely destroy the sample. However if the burst duration is kept extremely short, the various atomic components of the sample, although essentially exploding outward, will not have enough time to move significantly over the duration of the burst. Here extremely short bursts of coherent X-rays, often between about $10^{-13}$ seconds (100 femtoseconds) and $10^{-17}$ seconds (10 attoseconds), or even shorter are often preferred. Because softer X-rays are much less destructive, however, longer duration bursts may be used when soft X-ray lasers are used.

At least the first signal (data from the detectors 128) may then be used to determine the structure of the sample by any means desired. However in a preferred embodiment, the system will use at least one computer processor (132) to collect at least first signal data (128) pertaining to the location and intensity of these X-rays (112a, 112b), and reconstruct a likely representation of a structure of the microscopy sample at approximately a nanometer level of resolution (136). Here, "nanometer level" is typically between about 10 to 0.1 nanometers of resolution, or more broadly between about 20 to 0.01 nanometers of resolution.

Thus returning to FIGS. 1 and 4, and to reiterate, coherent X-rays are obtained from an X-ray port (see FIG. 4 402) and are focused and collimated by a first X-ray optical device (X-ray mirror) (102) and often an optional pinhole collimator (104). This pulse of focused coherent X-rays (106) is then used to illuminate one or more microscopy samples (108) that have been positioned with a sample administrator (110). The pinhole collimator is generally composed of an X-ray opaque material with a smaller pinhole. The X-ray opaque material blocks off-angle X-rays, and the pinhole generally only allows the collimated or focused X-rays to reach the sample (108).

Put alternatively, the at least one X-ray mirror (102) may be configured to work in conjunction with a pinhole collimator (104) to concentrate collimated coherent X-rays (106) onto the microscopy sample (108) on or positioned by the sample administrator (110).

As previously discussed, the sample administrator (110) can be anything from a pin used to place the sample (108) in the correct position, or it may be a more complex device, such as a sample injection port configured to dispense a plurality of small droplets of particles of sample into the vacuum chamber at the correct position and correct times. When the sample administrator is an injection port, the microscope may be configured to obtain data from a plurality of similar type samples, (e.g. a plurality of virus particles), and to use this data from a plurality of samples to deduce an average structure of the plurality of samples.

As previously discussed, some of the coherent X-rays are diffracted (112) or scattered (114), and the X-rays diffracted at greater angles convey information regarding the smaller scale details of the sample. Other coherent X-rays (114) are diffracted or scattered at smaller angles, while many X-rays pass completely through the sample (116). Thus the smaller angle X-rays (114) tend to be more useful for obtaining lower resolution imaging data (e.g. will report on the larger structural aspects of the sample), and at the same time, tend to be less useful for diffraction structure reconstruction purposes because of interference from the main X-ray beam (116).

As previously discussed, in a preferred embodiment of the invention, a more complex set of X-ray optical elements and detectors may be used. In this preferred embodiment, the detection apparatus may comprise at least a first outer portion (120, 120a) and a second inner portion (126 or 126a or 126b). This preferred embodiment will also comprise at least one additional second X-ray optical device (124, or 124a or 124b) configured to focus X rays diffracted or scattered from the sample (108) at smaller angles. This second X-ray optical device (124, 124a, 124b) will also reside inside vacuum chamber (400). It (124) focuses X-rays obtained from microscopy sample (108) onto a second inner portion of said detection apparatus (126, or 126a, or 126b), thereby producing a second signal from the second X-ray optical device.

Due to the X-ray focusing characteristics of the second X-ray optical device, this second signal is typically a magnified (but lower resolution) image of the sample (108), as is shown in (134). In this preferred embodiment, the at least one computer processor (132) will typically be further configured to use both the first signal (128) from the first outer portion of the detection device (120) as well as a second signal (130) from a second inner portion of the optical detection device (126) to reconstruct a likely representation of a structure of said microscopy sample at a nanometer level of resolution.

The X-rays diffracted at greater angles (112) by sample (108) can be detected by a first outer portion of an X-ray detection apparatus (120) without need of further X-ray focusing systems. However to make better use the smaller angle scattered or diffracted X-rays (114), a second X-ray optical device may be used. Although this second X-ray optical device may also be an X-ray mirror device, in a preferred embodiment, one or more nanometer scale X-ray zone plates (124) that focus least some of the narrower angle X-rays (114) onto a second inner portion of an X-ray detection apparatus (124) are preferred. These nanometer scale X-ray zone plates may be fabricated according to the methods of Sakdinawat and Chang, US patent publication 2015/0376798, the entire contents of which are incorporated herein by reference.

Briefly, these fabrication methods work by forming a metal pattern on a substrate surface, such as a silicon surface by forming hole concentration balancing structures onto the substrate proximal to this pattern. Then directionality controlled features are etched from the substrate surface into the substrate by metal-assisted chemical etching. The concentration of balancing structures is used to control the direction of these features. Alternative fabrication methods may also be used.

Put alternatively, in the example configuration shown in FIG. 1, the detection apparatus comprises a first outer portion (120) comprising a larger multi-pixel solid state X-ray detector configured to capture and detect most of the greater angle diffracted X-rays. Here this X-ray detector (120) (and often 126 as well) may comprise a plurality of spatially separated, solid state, detector elements.

In a preferred embodiment, this first outer portion of the detector (120) further comprises a central hole (122) or other type opening through which the narrower angle X-rays (114) and main X-ray beam (116) can pass. In this embodiment, on or near the central hole (122) (such as on the other side of the hole) is a second X-ray optical device, such as a nanometer scale zone plate device (124), as well as a second inner portion of the detection apparatus, (126). This second inner portion (126) can either also be a multi-pixel solid state X-ray detector as well (possibly with different characteristics), or alternatively can be a different type of X-ray detector device.

To illustrate the concepts in more detail, remember that as previously discussed, data (128) from both the first portion of the detection apparatus (120) and data (130) from the second portion of the apparatus (124) are sent to one or more computer processor(s) (132), which can use this data to reconstruct a representation of the structure of the microscopy sample.

In FIG. 1, as an example, assume that the microscopy sample (108) is that of an adenovirus, such as a type 5 adenovirus that, at a lower level of resolution (134), can be seen to have an overall icosahedral structure. At a higher level of resolution (136), as we go towards the nanometer level of resolution, we see that the adenovirus has an outer coat composed of hundreds of adenovirus capsomers, which in turn are composed of multimeric protomer proteins, each with a characteristic structure of amino acids arranged in polypeptide chains.

From an X-ray laser microscopy perspective, the higher resolution (e.g. nanometer level) aspects of the adenovirus structure (128, 136) will convey information pertaining to the internal structure of the various protomers, how these protomers in turn assemble into the capsomers, and the relative spacing of the capsomers. By contrast, the lower resolution aspects of the adenovirus structure will tend to convey information as to the overall icosahedral shape of the virus, and how the various capsomers assemble on a larger scale (130, 134). By using both types of information (130, 134) and (128, 136), the computer processor can produce a more accurate representation of the adenovirus sample (138) that incorporates both the detailed nanometer scale information pertaining to capsomer structure, as well as showing the overall icosahedral structure of the adenovirus as well.

Figure 2A:
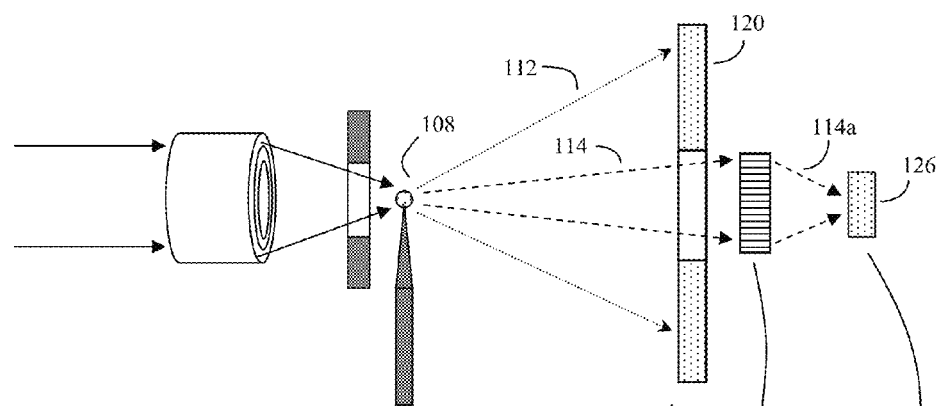
FIG. 2A shows a detail of some of the various X-ray laser microscopy components previously shown in FIG. 1.

FIG. 2A shows a detail of some of the various X-ray laser microscopy components previously shown in FIG. 1.

Figure 2B:
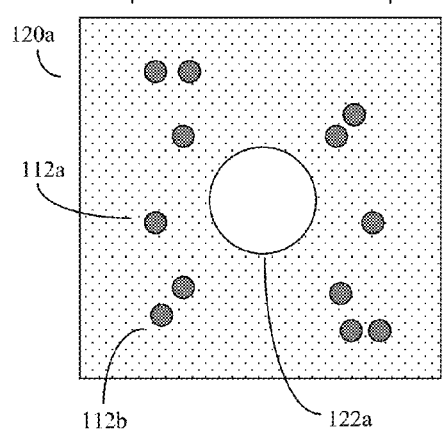
FIG. 2B, shows a drawing of the first outer portion of the X-ray detection apparatus as seen from an orthogonal angle.

FIG. 2B, shows a drawing of the first outer portion of the X-ray detection apparatus (120) as seen from an orthogonal angle (120a). Here various rays of X-ray light (112a, 112b) diffracted from the sample (108) hit the detection apparatus different locations and intensities, creating different patterns of diffraction spots (112a, 112b).

Figure 2C:
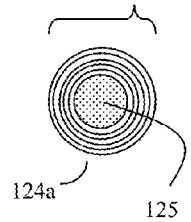
FIG. 2C shows a drawing of the second X-ray optical device (e.g. phase zone plate) as seen from an orthogonal angle.

FIG. 2C shows a drawing of the second X-ray optical device (e.g. phase zone plate) (124) as seen from an orthogonal angle (124a), as previously discussed. In some embodiments, this phase zone plate can be produced by high resolution nanofabrication methods. Here an example fabrication pattern showing various concentric patterns of etched rings is shown. Although in a preferred embodiment, the first X-ray optical device (102) is an X-ray mirror device, the inventors do not intend to exclude the possibility that the first X-ray optical device may also be one or more phase zone plates also produced by high resolution nanofabrication methods.

Note that as shown in FIG. 2C, the central portion (125) of the phase zone plate (124a) may be left solid (e.g. contain no rings, be left unetched) so as to protect the second inner portion of the detection apparatus (126) from the damaging effects of the undeflected X-rays (116).

Put alternatively, as previously discussed, the second X-ray optical device (124), as seen from this different angle (124a), is, in a preferred embodiment, at least one phase zone plate comprising a plurality of nanometer scale phase shifting zone structures configured to focus or collimate X-rays. In other embodiments, the first X-ray optical device (102) may be a similar type device.

In other embodiments, the at least one phase zone plate (124) can comprise one or more multi-layer Laue lenses, such as the lens structure described by H. C. Kang et al., "Nanometer Linear Focusing of Hard X Rays by a Multilayer Laue Lens" Phys. Rev. Letts. 96, 127401 (2006). Such multi-layer Laue lenses may, in some embodiments, may also be used to supplement or replace the first lens (102) or pinhole collimator (104) as well.

Figure 2D:
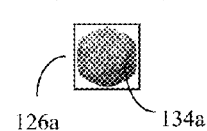
FIG. 2D shows a drawing of the second inner portion of the X-ray detection apparatus as seen from an orthogonal angle FIG. 3A again shows a detail of some of the various X-ray laser microscopy components previously shown in FIG. 1 and FIG. 2A.

FIG. 2D shows a drawing of the second inner portion of the X-ray detection apparatus (126) as seen from an orthogonal angle (126a). In this example, the second X-ray optical device has used some of the narrow angle X-rays (114) that have been focused (114a) by the second X-ray optical device (124), thus forming a magnified image (134a) of the microscopy sample (108).

As previously discussed, the various X-ray optical devices receive much energy from the X-ray beams, and thus are at risk for overheating. Thus in some embodiments, the at least one phase zone plate (124, 124a) may be further configured with at least one hollow channel where a cryogenic fluid, such as liquid helium, may circulate. This is shown in more detail in FIG. 3C.

Figure 3A:
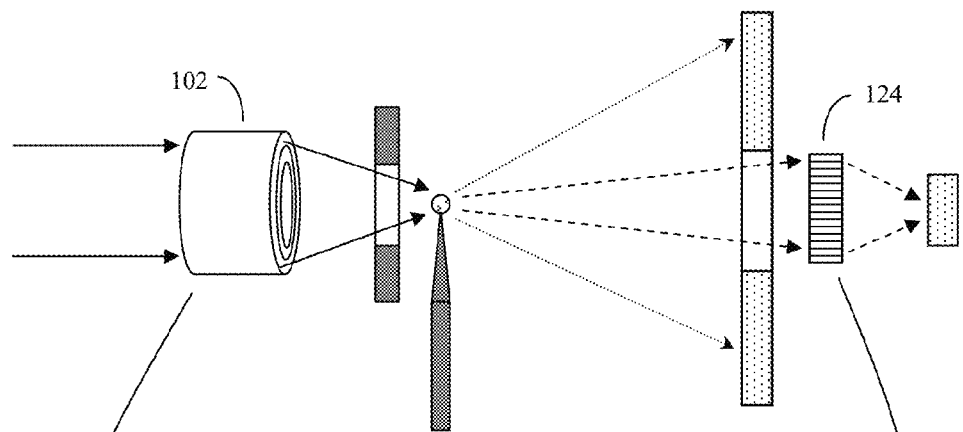
FIG. 3B shows that in some embodiments, the first X-ray optical device (e.g. the X-ray mirror device) may be cooled by running a low temperature fluid, such as liquid helium, through various hollow channels.
FIG. 3C shows that in some embodiments, the second X-ray optical device (e.g. the X-ray phase zone plate) may also be cooled by running a low temperature fluid, such as liquid helium, through various hollow channels.

FIG. 3A again shows a detail of some of the various X-ray laser microscopy components previously shown in FIG. 1 and FIG. 2A.

Figure 3B:
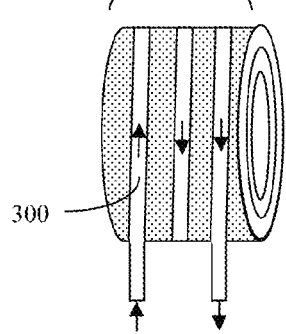

FIG. 3B shows that in some embodiments, the first X-ray optical device (102) (e.g. the X-ray mirror device) may be cooled by running a low temperature fluid, such as liquid helium, through various hollow channels (300) in the first X-ray optical device.

Figure 3C:
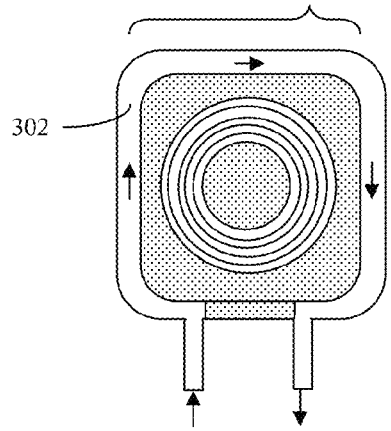

FIG. 3C shows that in some embodiments, the second X-ray optical device (124) (e.g. the X-ray phase zone plate) may also be cooled by running a low temperature fluid, such as liquid helium, through various hollow channels (302) in the second X-ray optical device.

In some embodiments, it may also be useful to cool the entire interior of the vacuum chamber (400) by running either regular fluids (such as water or refrigerant fluids such as tetrafluoroethane and/or Freon family fluids) or cryogenic fluids (such as liquid nitrogen or even liquid helium) though various interior channels (410) in the vacuum chamber walls. This is shown in FIG. 4.

FIG. 4 shows some additional components used in the improved X-ray laser microscopy method. In a preferred embodiment, components (102) to 126), previously shown in FIG. 1, may be placed inside of a vacuum chamber (400). The coherent X-rays (100) will enter into the vacuum chamber (400) through an X-ray port (402), typically comprised of an X-ray transparent material.

In a preferred embodiment, the vacuum chamber will maintain an ultra-low vacuum inside the chamber, such as a pressure of $10^{-9}$ Torr or less, and may optionally employ a sophisticated multiple stage vacuum pump system, such as the previously discussed three stage vacuum pump system (404), (406), (408), to do this.

Figure 5A:
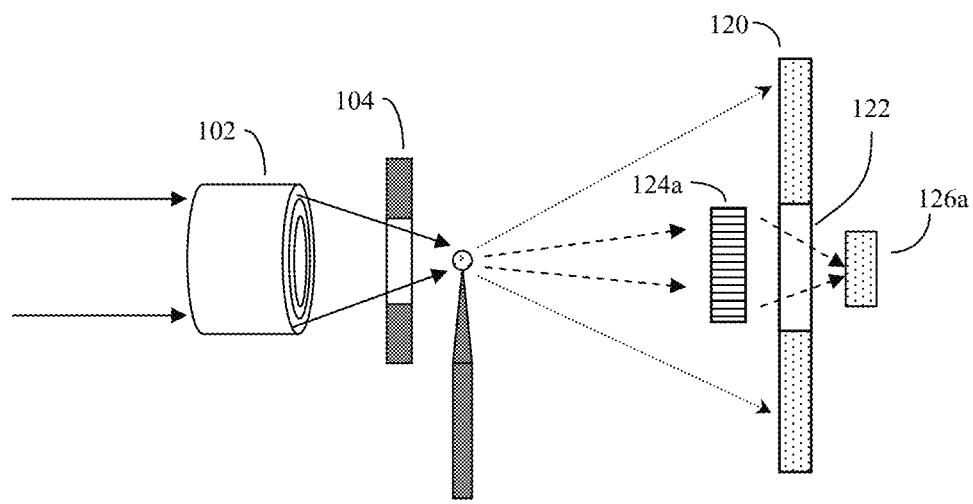
FIG. 5A shows an alternative embodiment where the second X-ray optical device (phase zone plate) and the second inner portion of the detection apparatus are disposed in a first alternative configuration

FIG. 5A shows an alternative embodiment where the second X-ray optical device (phase zone plate) (124) and the second inner portion of the detection apparatus (126) are disposed in a first alternative configuration with respect to the first outer portion of the detection apparatus (120) and optional hole (122). Here the second X-ray optical device (124a) is placed in front of the first outer portion of the detection apparatus (120), but the second inner portion of the detection apparatus (126a) is still placed behind hole (122).

Figure 5B:
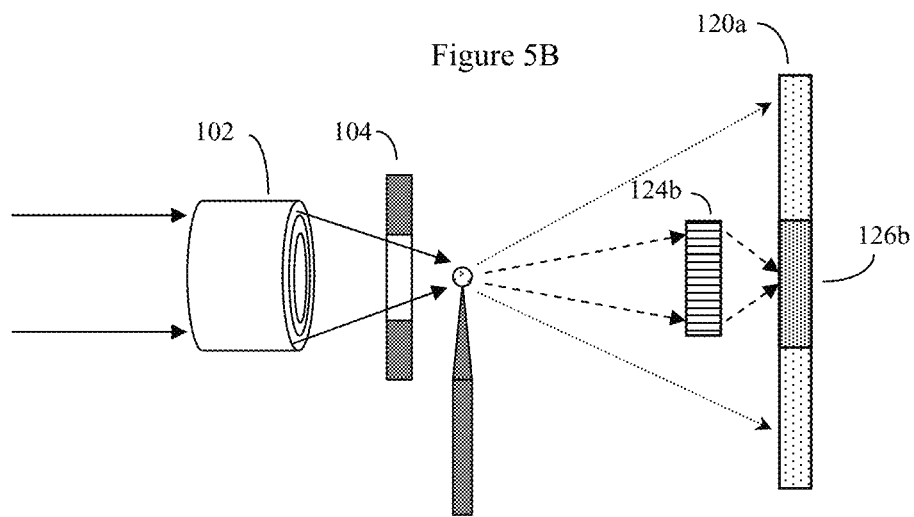
FIG. 5B shows a different alternative embodiment where the second X-ray optical device (phase zone plate) and the second inner portion of the optical detection apparatus are disposed in a second alternative configuration.

FIG. 5B shows a different alternative embodiment where the second X-ray optical device (phase zone plate) (124) and the second inner portion of the optical detection apparatus (126) are disposed in a second alternative configuration with respect to the first outer portion of the detection apparatus (120) and optional hole (122). Here the second X-ray optical device (124b) is placed in front of the first outer portion of the detection apparatus (120a), and the second inner portion of the detection apparatus (126b) is in the same plane as the first outer portion of the detection apparatus (120). In this embodiment, there is no hole (122).

Other Embodiments:

In some embodiments, as shown in FIGS. 1-5B, the first X-ray optical device (102) (e.g. the at least one X-ray mirror) may be entirely external to the pinhole opening in the pinhole collimator (104). However other embodiments are possible. In an alternative embodiment, however, the at least one X-ray mirror may be disposed in, or comprise, the pinhole aperture region (hole) of the pinhole collimator (104).

In some alternative embodiments, both the first X-ray optical device (102) and the second X-ray optical device (124) can be either two phase zone plates (e.g. both configured as per 124a) or two mirror/collimator devices (e.g. both configured as per 102/104). In other alternative embodiments, the first X-ray optical device (102) may be a phase zone plate, and the second X-ray optical device may be a mirror/collimator device (e.g. configured as per 102/104).

In some alternative embodiments, any or all surfaces that receive X-ray photons (radiation) may be coated with suitable X-ray resistant material, such as silicon, boron, silicon triboride, or other X-ray resistant material.

Software methods: In some embodiments, it may be useful to configure the at least one computer processor (132) to use various machine learning methods or neural network methods (e.g. deep neural networks, deep learning methods), to analyze both the X-ray diffraction data (128, 136) as well as X-ray imaging data (130, 134) and deduce an overall composite structure (138) of the sample (108). This overall structure will thus combine both sets of data (128, 130) to create a most likely structure (138) that is consistent with the combined data sources. Here, software libraries such as Caffe (developed by Berkeley Vision and Learning center), TensorFlow (developed by Google), and the like may be used.

Alternative Sample Handling Devices And Methods

Figure 6:
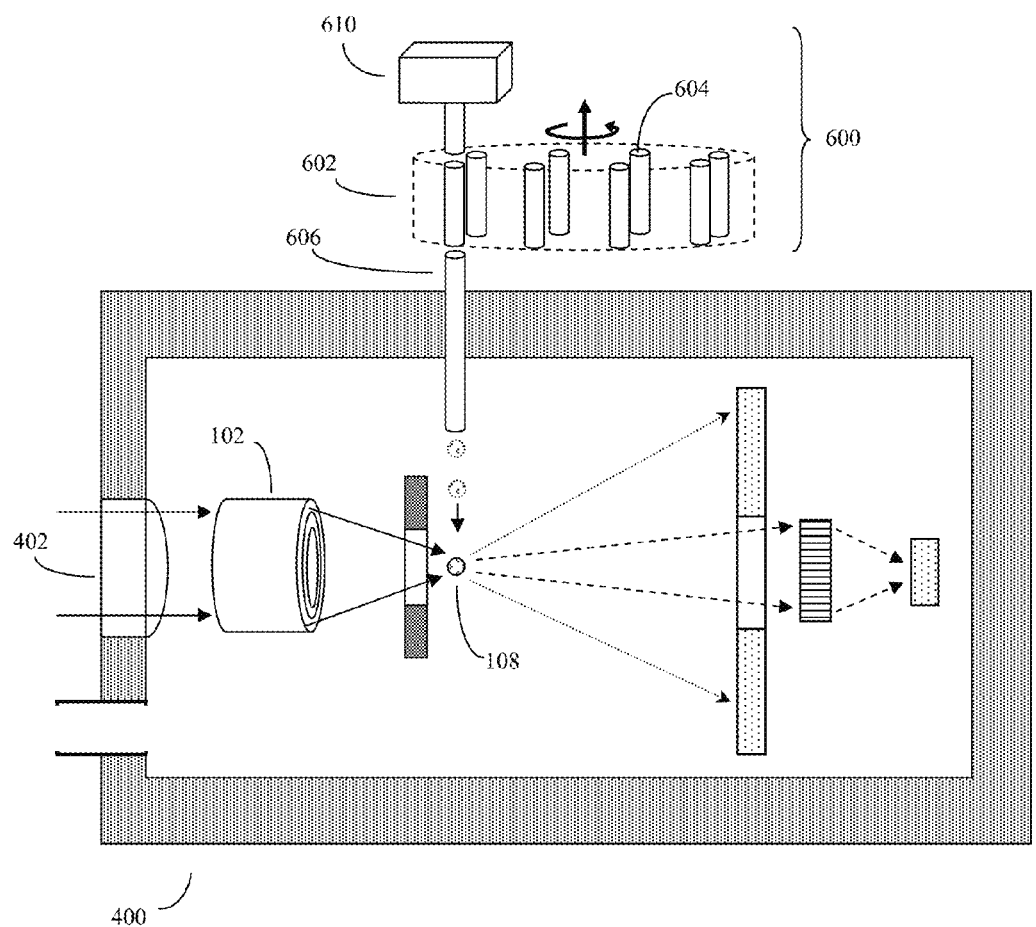
FIG. 6 shows a first alternative method of sample handling.

FIG. 6 shows a first alternative method of sample handling.

In this first alternative method, the sample administrator (600) can comprise a revolving multiple container sample holder (602) disposed either internal or external the vacuum chamber (400) (FIG. 6 shows an external configuration). Here the term container means that that there are individual chambers or spaces in the sample holder that can hold a given microscopy sample for at least a short duration of time. Although this container will usually have at least some walls, not all walls of the container need be sealed. Indeed in some embodiments, the container may be, for example, a cylinder with one or more open sides (e.g. top and bottom of the cylinder) open to facilitate sample entry, manipulation, and exit. In some cases, entry and exit of the sample into the container may be controlled by various valves, actuators, and the like.

In a preferred embodiment, each individual (separate) container (604) of this multiple chamber sample holder (602) can be configured to hold a separate microscopy sample (108), such as a different molecule. This separate microscopy sample can be either a different type of microscopy sample (e.g. different types of molecules), or separate versions (e.g. multiple versions) of the same type of sample (e.g. multiple specimens of the same type of molecule).

This first alternative method will typically also use a rotation mechanism (not shown) to control the disposition of the various samples. This rotation mechanism can comprise one or more actuators, often electronically controlled actuators such as motors, solenoids, valves and the like, and often will be processor controlled to administer various microscopy samples according to a scheme set up by the microscope's user. The rotation mechanism controls which sample will be analyzed at any given time, and here the operation of the rotation mechanism will be termed a "rotation operation".

In this embodiment, rotation operations on the revolving multiple container sample holder (602) in turn cause any one of the individual containers (604) to align with a common sample injection port (606). In a preferred embodiment, this alignment will be done in such a way as to avoid cross-contamination between different types of samples. This can be done by small gaps between the containers (604) and the common port (606), use of cleaning mechanisms between samples, and the like.

As a result, possibly facilitated by an injection mechanism (e.g. a device 610 to inject the given microscopy sample into proper portion of the vacuum chamber), the separate microscopy samples (108) from the separate individual containers (604) are injected into the proper region of the vacuum chamber (400) (e.g. into the region where the first X-ray optical device (102) can focus and/or collimate the burst of coherent X-rays onto the microscopy sample (108)), often by way of the common sample injection port (606).

Figure 7:
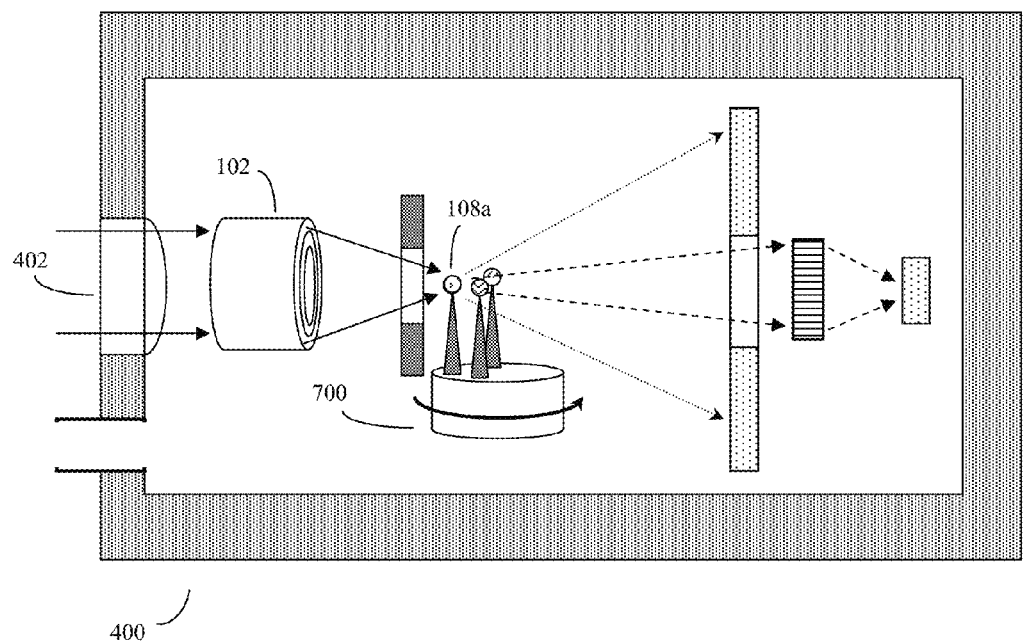
FIG. 7 shows a second alternative method of sample handling.

FIG. 7 shows a second alternative method of sample handling.

In this second alternative method, the "sample administrator" can comprise a revolving multiple-sample holder (700), often disposed internal to the vacuum chamber (400). Here separate (again this can be either different types of samples, or multiple versions of the same type of sample) microscopy samples (exemplified by 108a) are disposed on different locations of this revolving multiple-sample holder (700). The motion of this sample holder can also be controlled by various electromechanical actuators, such as motors, solenoids and the like, often also under processor control. These motions will again be termed "rotation operations".

In this second alternative method, rotation operations on the revolving multiple-sample holder (700) cause any one of the separate microscopy samples to be properly positioned for microscopy. Here, again, this will usually be in a position where the first X-ray optical device (102) can focus and/or collimate a burst of coherent X-rays onto any one of the different microscopy samples (108a), as selected by the user of the microscope.

In some embodiments, it may be useful to control the dimensions of the revolving multiple-sample holder and/or to incorporate X-ray shielding so that samples other than (108a) that are not being observed are protected from damage while, for example, sample (108a) is being analyzed.

Figure 8:
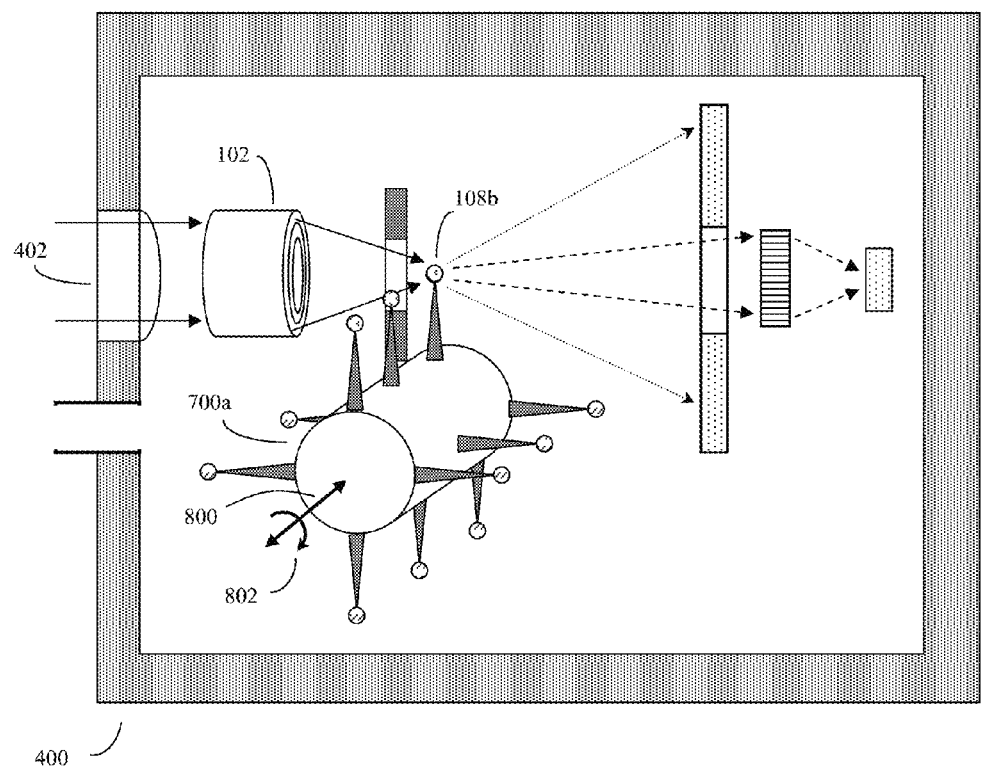
FIG. 8 shows a third alternative method of sample handling.

FIG. 8 shows a third alternative method of sample handling.

This third alternative method of sample handling can be viewed as being an extension of the second alternative method discussed above. In this third alternative method, the revolving multiple sample holder (700a) (compare with 700 in FIG. 7) further comprises any of a second axis of rotation and/or a second linear position axis (800).

Here any of these second axis of rotation or second linear position (800), as well as rotation (802) operations on the revolving multiple sample holder (700a), can cause any one of the separate microscopy samples (108b) to be properly positioned (e.g. so that the first X-ray optical device 102 can focus and/or collimate the burst of coherent X-rays onto any one of the different microscopy samples 108b). Although FIG. 8 (802) shows an embodiment where the multiple sample holder is a cylinder, other shapes, such as spheres, cubes, may also be used. The general idea is simply that the sample holder be configured so that it holds a plurality of samples, and that at least two degrees of movement or rotation may be required to properly position a given microscopy sample. In some embodiments, additional shielding may be employed (not shown) to help protect at least some of the samples from the harmful effect of the X-rays when the samples are not being observed or analyzed by the X-ray microscope.

Figure 9A:
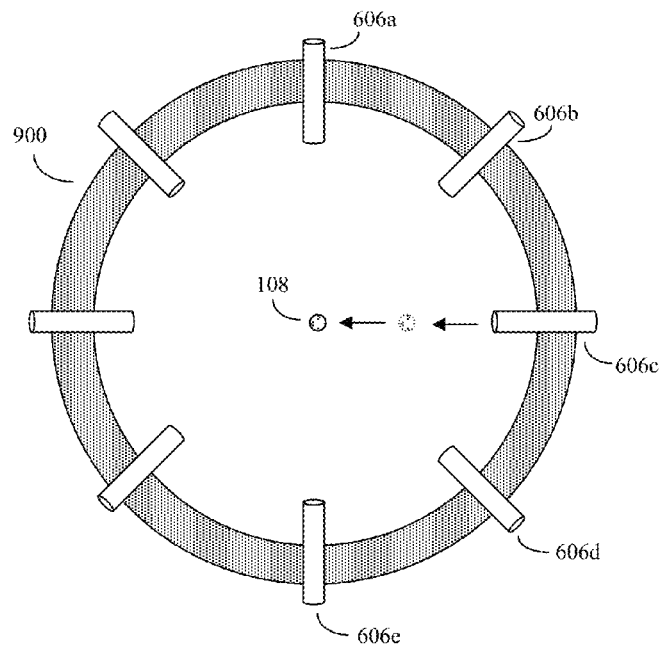
FIG. 9A shows a front view of a device useful for a fourth alternative method of sample handling.

FIG. 9A shows a front view of a device useful for a fourth alternative method of sample handling.

Figure 9B:
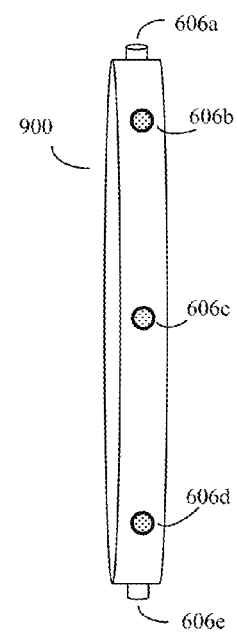
FIG. 9B shows a side view of the device from FIG. 9A.
Figure 9C:
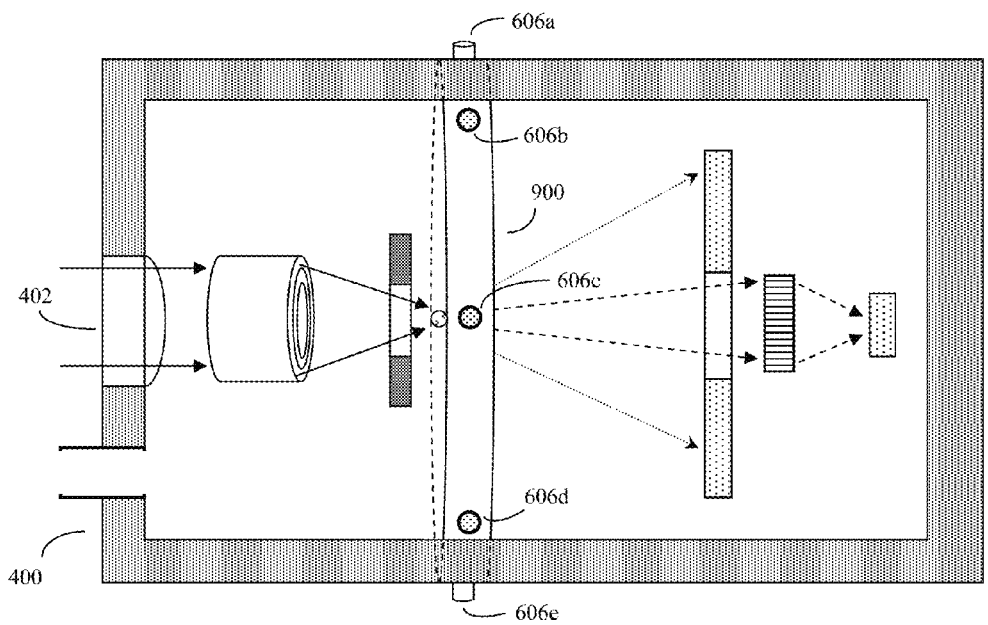
FIG. 9C shows the device from FIG. 9A and 9B in the context of the microscope's vacuum chamber.

In this fourth alternative method of sample handling, the sample administrator can comprise a plurality of injection ports (e.g. 606a ... 606e), often disposed around a perimeter of the vacuum chamber (400). In FIGS. 9A-9C, these various sample ports are shown disposed in a ring (900) that can, for example form part of the vacuum chamber wall, but other configurations may also be used. Here any individual injection port (e.g. any one of 606a ... 606e) from this plurality of injection ports (606a ... 606e) can be configured to handle a separate microscopy sample (108), and to inject these separate microscopy samples into the vacuum chamber (400) at the proper position for viewing by the microscope. As before, these separate microscopy samples can be different types of samples, or multiple versions of the same type of sample.

FIG. 9B shows a side view of the device from FIG. 9A.

FIG. 9C shows the device from FIG. 9A and 9B in the context of the microscope's vacuum chamber.

Figure 10:
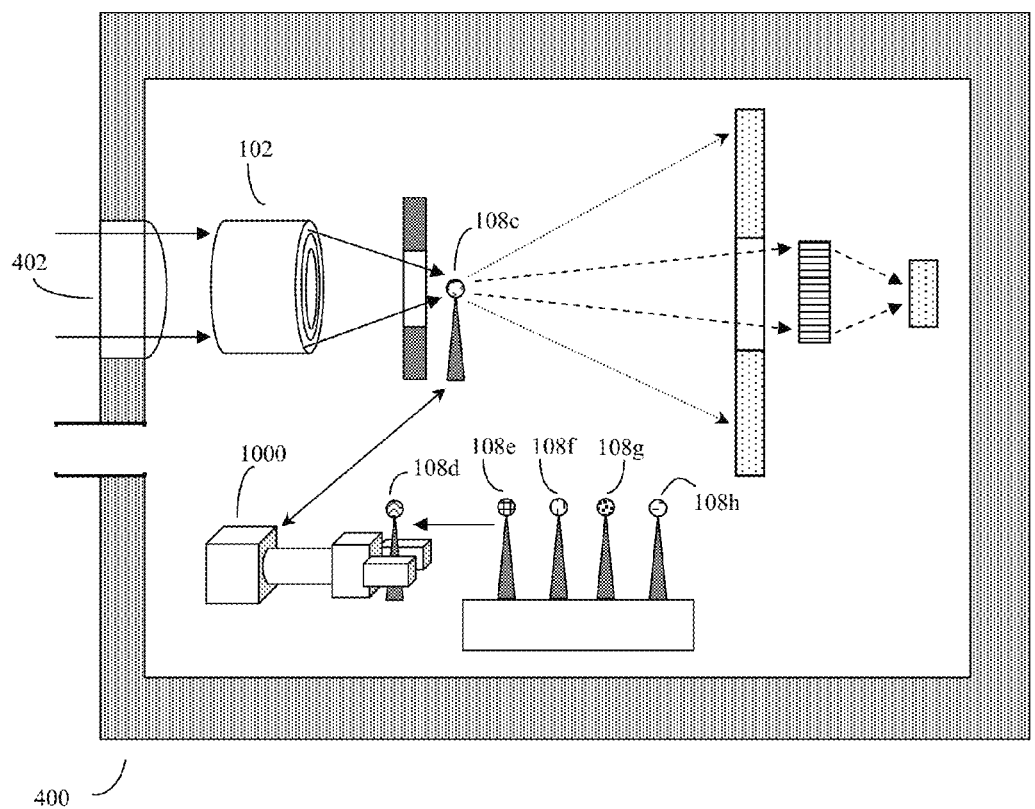
FIG. 10 shows a fifth alternative method of sample handling.

FIG. 10 shows a fifth alternative method of using the microscope to analyze a plurality of samples. Here the sample administrator can comprise a plurality of sample holders (108*c*, 108*d,* 108*e*, 108*f,* 108*g*, and 108*h*) disposed inside the vacuum chamber (400). Each sample holder will typically be configured to hold a separate microscopy sample. This method uses a robotic sample holder and movement apparatus (1000) (e.g. a robotic hand or arm configured to capture, move, and then release the various sample holders 108*c* . . . 108*h*).

This robotic sample holder and movement apparatus (1000) is often also controlled by various electromagnetic actuators and optional processor control. The movement apparatus can be used to move any one of the various plurality of sample holders (e.g. 108*c*) from a storage position into a proper position for microscopic analysis. As before, this proper position for microscopic analysis will typically be where the first X-ray optical device (102) can focus and/or collimate the burst of coherent X-rays onto any one of the different microscopy samples.

As before, in some embodiments, it may be useful to control the dimensions and/or location of the storage position sample holder and/or to incorporate X-ray shielding so that samples such as (108*d* . . . 108*h*), that are not being observed, are protected from damage while, for example, sample (108*c*) is being analyzed.

The invention claimed is:

1. An X-ray laser microscopy method, said method comprising:
    obtaining an X-ray port capable of supplying a coherent source of X-ray illumination;
    obtaining a first X-ray optical device configured to focus and/or collimate X-rays;
    obtaining a sample administrator, detection apparatus, and vacuum chamber, wherein said X-ray port, first X-ray optical device, and at least a portion of said sample administrator are disposed inside said vacuum chamber so that said first X-ray optical device is in between said X-ray port and at least one microscopy sample applied by said sample administrator, and said at least one microscopy sample applied by said sample administrator is substantially in between said first X-ray optical device and said detection apparatus;
    wherein said sample administrator comprises a plurality of injection ports disposed around a perimeter of said vacuum chamber;
    wherein each individual injection port of said plurality of injection ports is configured to handle a separate microscopy sample, and to inject said separate microscopy samples into said vacuum chamber;
    wherein said detection apparatus comprises at least a first outer portion;
    reducing pressure in said vacuum chamber to a pressure of $10^{-9}$ Torr or less and
    using said sample administrator to control a position of a said at least one microscopy sample;
    chilling said first X-ray optical device to temperatures of 20 degrees Kelvin or less;
    using said X-ray port to provide a burst of coherent X-rays, and using said first X-ray optical device to focus and/or collimate said burst of coherent X-rays onto said at least one microscopy sample positioned by said sample administrator;
    using at least a first portion of said detection apparatus to detect a first signal comprising spatially separated X-rays that have been diffracted at various angles from said at least one microscopy sample; and
    using at least one computer processor and said first signal to reconstruct a likely representation of a structure of said at least one microscopy sample at a nanometer level of resolution;
    wherein said vacuum chamber comprises walls configured with interior channels, and further cooling said vacuum chamber by circulating a fluid through said interior channels.

2. The method of claim 1, wherein said detection apparatus comprises at least said first outer portion and a second inner portion, further obtaining a second X-ray optical device configured to focus X rays, disposing said second X-ray optical device inside said vacuum chamber, and using said second X-ray optical device to focus X-rays obtained from said at least one microscopy sample onto a second inner portion of said detection apparatus, thereby producing a second signal from said second X-ray optical device; and
    wherein said at least one computer processor is further configured to use both said first signal and said second signal to reconstruct a likely representation of a structure of said at least one microscopy sample at a nanometer level of resolution.

3. The method of claim 1, further using a three stage vacuum pump to reduce the pressure in said vacuum chamber to a pressure of $10^{-13}$ Torr or less.

4. The method of claim 1, wherein said burst of coherent X-rays has a time duration between $10^{-13}$ seconds (100 femtoseconds) and $10^{-17}$ seconds (10 attoseconds).

5. The method of claim 2, wherein any of said first or second X-ray optical devices comprises at least one phase zone plate comprising a Multilayer Laue Lens or other plurality of nanometer scale phase shifting zones structures configured to focus or collimate X-rays.

6. The method of claim 2, wherein at least said first X-ray optical device comprises at least one X-ray mirror formed from a plurality of curved X-ray reflecting surfaces, said x-ray mirror comprising any of a Wolter, Kirkpatrick-Baez, or Schwarzschild x-ray mirror design.

7. The method of claim 5, wherein at least one said one phase zone plate is further configured with at least one hollow channel, further circulating liquid helium through said at least one hollow channel.

8. The method of claim 6, wherein at least one X-ray mirror is configured to work in conjunction with a pinhole collimator to concentrate collimated coherent X-rays onto said at least one microscopy sample applied by said sample administrator.

9. The method of claim 8, wherein said at least one X-ray mirror is entirely external to said pinhole collimator, or wherein at least one X-ray mirror of said at least one X-ray mirror is disposed in a pinhole aperture region (hole) of said pinhole collimator.

10. The method of claim 8, wherein said at least one X-ray mirror or at least one phase zone plate comprises any of silicon, boron, and silicon triboride.

11. An X-ray laser microscopy method, said method comprising:
    obtaining an X-ray port capable of supplying a coherent source of X-ray illumination;
    obtaining a first X-ray optical device configured to focus and/or collimate X-rays;
    obtaining a sample administrator, detection apparatus, and vacuum chamber, wherein said X-ray port, first X-ray optical device, and at least a portion of said sample administrator are disposed inside said vacuum chamber so that said first X-ray optical device is in between said X-ray port and at least one microscopy sample applied by said sample administrator, and said at least one microscopy sample applied by said sample administrator is substantially in between said first X-ray optical device and said detection apparatus;

wherein said sample administrator comprises a plurality of injection ports disposed around a perimeter of said vacuum chamber;

wherein each individual injection port of said plurality of injection ports is configured to handle a separate microscopy sample, and to inject said separate microscopy samples into said vacuum chamber;

wherein said detection apparatus comprises at least a first outer portion;

reducing pressure in said vacuum chamber to a pressure of $10^{-9}$ Torr or less and using said sample administrator to control a position of a said at least one microscopy sample;

chilling said first X-ray optical device to temperatures of 20 degrees Kelvin or less;

using said X-ray port to provide a burst of coherent X-rays, and using said first X-ray optical device to focus and/or collimate said burst of coherent X-rays onto said at least one microscopy sample positioned by said sample administrator;

using at least a first portion of said detection apparatus to detect a first signal comprising spatially separated X-rays that have been diffracted at various angles from said at least one microscopy sample;

using at least one computer processor and said first signal to reconstruct a likely representation of a structure of said at least one microscopy sample at a nanometer level of resolution;

wherein said vacuum chamber comprises walls configured with interior channels, and further cooling said vacuum chamber by circulating a fluid through said interior channels; and wherein said burst of coherent X-rays has a time duration between $10^{-13}$ seconds (100 femtoseconds) and $10^{-17}$ seconds (10 attoseconds).

12. The method of claim 11, wherein said detection apparatus comprises at least said first outer portion and a second inner portion, further obtaining a second X-ray optical device configured to focus X rays, disposing said second X-ray optical device inside said vacuum chamber, and using said second X-ray optical device to focus X-rays obtained from said at least one microscopy sample onto a second inner portion of said detection apparatus, thereby producing a second signal from said second X-ray optical device; and wherein said at least one computer processor is further configured to use both said first signal and said second signal to reconstruct a likely representation of a structure of said at least one microscopy sample at a nanometer level of resolution; and wherein any of said first or second X-ray optical devices comprises at least one phase zone plate comprising a Multilayer Laue Lens or other plurality of nanometer scale phase shifting zones structures configured to focus or collimate X-rays.

13. An X-ray laser microscopy method, said method comprising:

obtaining an X-ray port capable of supplying a coherent source of X-ray illumination;

obtaining a first X-ray optical device configured to focus and/or collimate X-rays;

obtaining a sample administrator, detection apparatus, and vacuum chamber, wherein said X-ray port, first X-ray optical device, and at least a portion of said sample administrator are disposed inside said vacuum chamber so that said first X-ray optical device is in between said X-ray port and at least one microscopy sample applied by said sample administrator, and said at least one microscopy sample applied by said sample administrator is substantially in between said first X-ray optical device and said detection apparatus;

wherein said sample administrator comprises a revolving multiple container sample holder disposed external to said vacuum chamber;

wherein each separate container of said multiple container sample holder is configured to hold a separate microscopy sample;

wherein rotation operations on said revolving multiple container sample holder cause any one of said separate containers to align with a common sample injection port; and wherein separate microscopy samples from different said separate containers are injected into said vacuum chamber through said common sample injection port;

wherein said detection apparatus comprises at least a first outer portion;

reducing pressure in said vacuum chamber to a pressure of $10^{-9}$ Torr or less and using said sample administrator to control a position of a said at least one microscopy sample;

chilling said first X-ray optical device to temperatures of 20 degrees Kelvin or less;

using said X-ray port to provide a burst of coherent X-rays, and using said first X-ray optical device to focus and/or collimate said burst of coherent X-rays onto said at least one microscopy sample positioned by said sample administrator;

using at least a first portion of said detection apparatus to detect a first signal comprising spatially separated X-rays that have been diffracted at various angles from said at least one microscopy sample; and using at least one computer processor and said first signal to reconstruct a likely representation of a structure of said at least one microscopy sample at a nanometer level of resolution;

wherein said vacuum chamber comprises walls configured with interior channels, and further cooling said vacuum chamber by circulating a fluid through said interior channels.

14. The method of claim 13, wherein said detection apparatus comprises at least said first outer portion and a second inner portion, further obtaining a second X-ray optical device configured to focus X rays, disposing said second X-ray optical device inside said vacuum chamber, and using said second X-ray optical device to focus X-rays obtained from said at least one microscopy sample onto a second inner portion of said detection apparatus, thereby producing a second signal from said second X-ray optical device; and wherein said at least one computer processor is further configured to use both said first signal and said second signal to reconstruct a likely representation of a structure of said at least one microscopy sample at a nanometer level of resolution.

15. The method of claim 13, further using a three stage vacuum pump to reduce the pressure in said vacuum chamber to a pressure of $10^{-13}$ Torr or less.

16. The method of claim 13, wherein said burst of coherent X-rays has a time duration between $10^{-13}$ seconds (100 femtoseconds) and $10^{-17}$ seconds (10 attoseconds).

17. The method of claim 14, wherein any of said first or second X-ray optical devices comprises at least one phase zone plate comprising a Multilayer Laue Lens or other plurality of nanometer scale phase shifting zones structures configured to focus or collimate X-rays.

18. The method of claim 14, wherein at least said first X-ray optical device comprises at least one X-ray mirror formed from a plurality of curved X-ray reflecting surfaces, said x-ray mirror comprising any of a Wolter, Kirkpatrick-Baez, or Schwarzschild x-ray mirror design.

19. The method of claim 18, wherein said at least one X-ray mirror is configured to work in conjunction with a pinhole collimator to concentrate collimated coherent X-rays onto said at least one microscopy sample applied by said sample administrator.

20. The method of claim 19, wherein said at least one X-ray mirror is entirely external to said pinhole collimator, or wherein at least one X-ray mirror of said at least one X-ray mirror is disposed in a pinhole aperture region (hole) of said pinhole collimator.

\* \* \* \* \*